United States Patent [19]

Klein

[11] Patent Number: 5,203,694
[45] Date of Patent: Apr. 20, 1993

[54] ANATOMICAL HEAD-WORN DEVICE FOR APPLYING ORTHODONTIC FORCE

[76] Inventor: Paul E. Klein, 928 Lake Shore Rd., Lake Oswego, Oreg. 97034

[21] Appl. No.: 839,630

[22] Filed: Feb. 20, 1992

[51] Int. Cl.$^5$ .............................................. A61C 3/00
[52] U.S. Cl. ........................................ 433/5; 2/171.2
[58] Field of Search ................ 433/5; 2/171.2, 185 R, 2/188

[56] References Cited

U.S. PATENT DOCUMENTS

| | | | |
|---|---|---|---|
| 415,829 | 11/1889 | Angle | 433/5 |
| 523,192 | 7/1894 | Angle | 433/5 |
| 3,186,089 | 6/1965 | Asher | 433/5 |
| 3,401,457 | 9/1968 | Hickham | 433/5 |
| 3,423,832 | 1/1969 | Nelson | 433/5 |
| 3,437,339 | 4/1969 | Starck | 2/185 R |

OTHER PUBLICATIONS

*Great Lakes Ortho Ltd.*, Sep. 1991 Catalog *Malocclusion of the Teeth*, E. H. Angle, published 1907 pp. 88 and 192.

*Primary Examiner*—John J. Wilson
*Attorney, Agent, or Firm*—Kolisch, Hartwell, Dickinson, McCormack & Heuser

[57] ABSTRACT

An anatomical head-worn device is provided in the form of a bill cap, also known as a baseball cap. The cap includes one or more tension-device anchors for accommodating the attachment of orthodontic tension-applying devices used to direct tension force to selected parts of the head and mouth. The orthodontic forces are reacted against the head via the cap. The cap, when fitted snugly on the head, serves as a stable force base for applying forces in different directions on each side of the head. In one embodiment, tension-device anchors are mounted on the sides of the dome of the cap. In another embodiment, a downwardly-depending arm is supported on the bill of the cap. The arm extends in front of the face, and provides an anchor point for the application of protractive orthodontic foces. Use of an elastomeric orthodontic tension-applying device with the rigid arm extending in front of the face is also disclosed, including systems for non-positive engagement between the tension-applying device and the rigid arm. The non-positive engagement permits the instant release of orthodontic tension force if a mishap should occur which might otherwise injure the wearer. A releasable hook for securing a tension-applying device to only one side of the downwardly depending arm is also disclosed. In yet another embodiment of the cap, the tension-device anchors are mounted on the bill of the cap, which can then be worn backwards on the head to apply retractive orthodontic forces. The use of a bill cap makes the wearing of exterior orthodontic devices more socially acceptable to children and others, encouraging the user to accept needed orthodontic corrections.

23 Claims, 3 Drawing Sheets

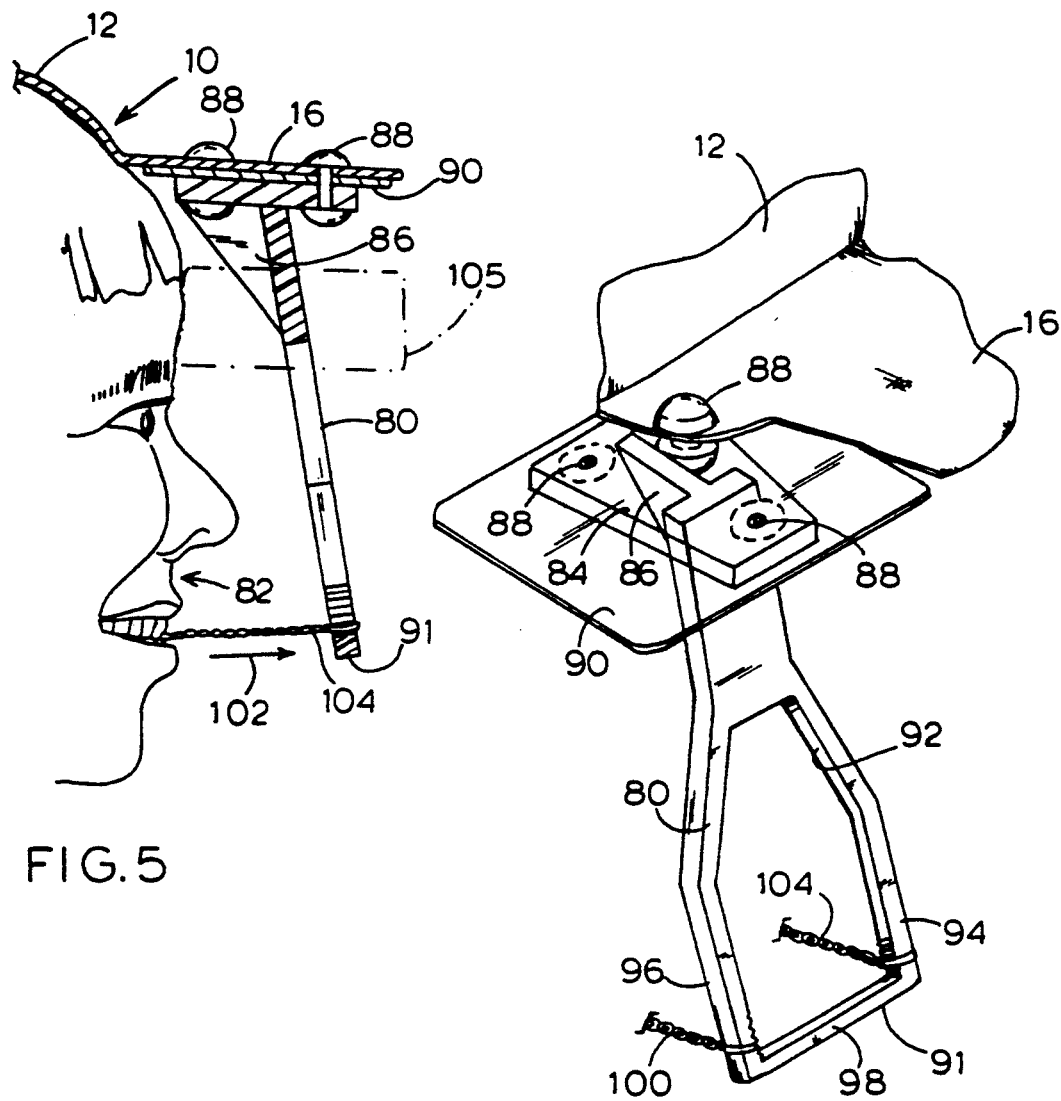
FIG. 5
FIG. 6
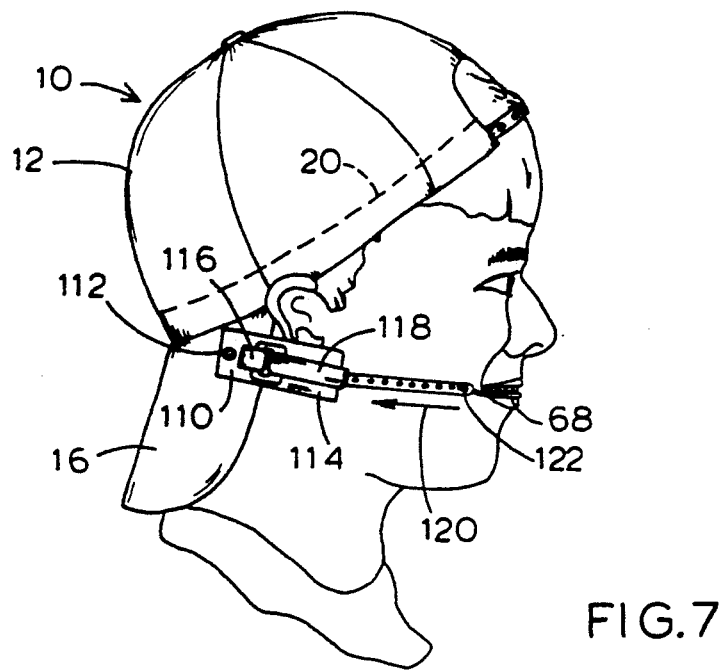
FIG. 7

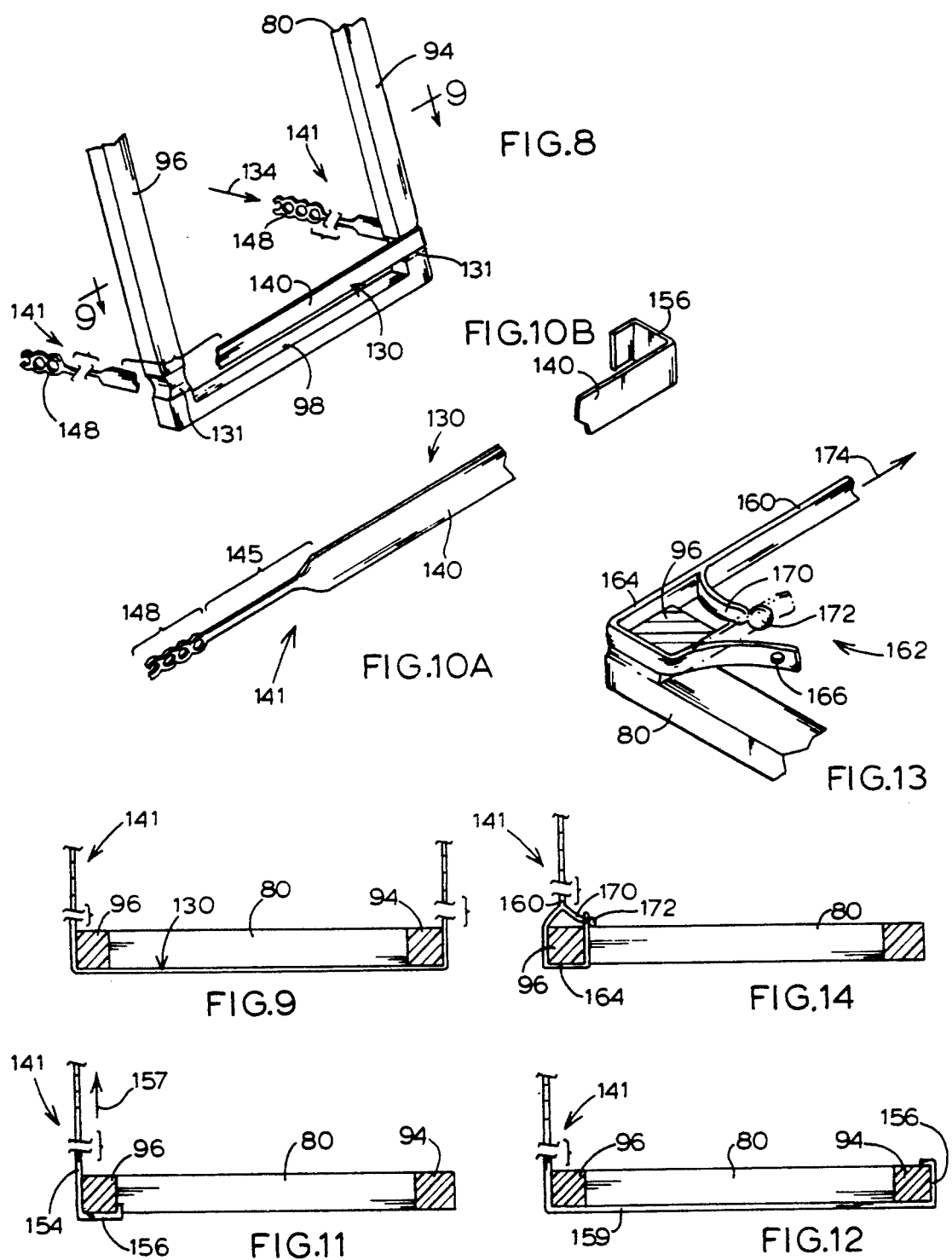

ANATOMICAL HEAD-WORN DEVICE FOR APPLYING ORTHODONTIC FORCE

BACKGROUND AND SUMMARY OF THE INVENTION

The invention relates to orthodontic products, and particularly to a head-worn device for applying orthodontic tension force.

Various kinds of externally-worn orthodontic devices are available for applying orthodontic tension forces to selected areas of the head and mouth. Some devices extend around the back of the head to apply a retractive orthodontic force which is reacted against the back or top of the head. Other devices apply protractive orthodontic forces by means of a face mask, which react against the chin, forehead or other parts of the face. Prior art external orthodontic devices or appliances are generally unattractive to the children and others who must wear them, increasing the resistance to their use.

In addition to the problem of the unattractive medical appearance of prior art external orthodontic devices, they generally can only apply forces which balance on either side of the head. That is because if tension is applied on one side of the head, a similar tension must be applied on the opposite side to keep the device from shifting position-for example, rotating. It is not possible for prior art devices to direct highly unbalanced forces selectively, such as a retractive force on one side of the mouth and a protractive force on the other side of the mouth. Yet such selective application of differently-directed tension forces is sometimes orthodontically necessary. Consequently, the provision of an orthodontic device capable of such selective-force applications would be desirable.

It would be advantageous, too, to have an attractive and more socially acceptable type of external orthodontic force-applying device.

It would also be advantageous to have an orthodontic device capable of applying orthodontic tension forces selectively in different directions on different sides of the head and mouth.

Accordingly, the present invention provides an anatomical head-worn device for application of an orthodontic tension force. The device takes the form of a bill cap with a dome for covering the top of the head and a bill extending outwardly from the dome along a portion of its perimeter. The cap is sized to fit snugly against the head to inhibit rotational slippage relative to the head. A tension-device anchor is provided on the cap for accommodating the attachment thereto of an orthodontic tension-applying device in a manner which causes the orthodontic force applied to be reacted against the head via the cap.

In one preferred form of the invention, a load-bearing strap is mounted on the cap within the dome for reactive force engagement with the head in a manner non-deforming to the dome. The tension-device anchors are mounted on the cap in a manner which causes the reactive forces to be applied predominately against the load-bearing strap.

In another preferred form of the invention, the tension-device anchor is in the form of a rigid arm mounted on the bill of the cap. The arm extends downwardly in front of the face, when the cap is worn with the bill extending forwardly, and accommodates attachment of orthodontic tension-applying devices thereto. An orthodontic force applied in that manner is reacted against the head via the rigid arm, the bill and the cap.

In still a further alternative form of the invention, the tension-device anchors are mounted on the bill of the cap for use when the cap is worn backwards, i.e., with the bill extending rearwardly.

BRIEF DESCRIPTION OF THE DRAWINGS

FIG. 5 is a partial, partially cross-sectional, side-elevational view of an alternative embodiment of the anatomical head-worn device of the invention, showing a rigid arm mounted on the bill of the cap for extending downwardly in front of the face.

FIG. 6 is a partial, perspective view, enlarged and partially cut away, showing the rigid arm and arm mounting system of the embodiment of FIG. 5.

FIG. 7 is a side elevational view, as in FIG. 1, illustrating another alternative embodiment of the anatomical head-worn device incorporating tension-device anchors on the bill portion of the cap.

FIG. 8 is a partial, perspective view, partially cut away, of the lower portion of the rigid arm shown in FIGS. 5 and 6, illustrating an alternative embodiment of the invention which includes an elastomeric tension-applying device which is non-positive-engaging with the rigid arm shown in FIGS. 5 and 6.

FIG. 9 is a partial, cross-sectional view of the rigid arm and tension-applying device shown in FIG. 8, taken along line 9—9 of FIG. 8.

FIG. 10A is a partial perspective view of the terminal end of an elastomeric orthodontic tension-applying device, the terminal end being used in the tension-applying devices shown in FIGS. 8–14.

FIG. 10B is a partial, perspective view of an integral hook formed on the securing end of the elastomeric tension-applying device shown in FIGS. 11 and 12, the hook being combined with the terminal end portion shown in FIG. 10A to form the embodiments illustrated in FIGS. 11 and 12.

FIG. 11 is a top cross-sectional view as in FIG. 9 showing the non-positive engagement between an elastomeric tension-applying device incorporating the parts illustrated in FIGS. 10A and 10B with the rigid arm shown in FIGS. 5 and 6.

FIG. 12 is a top cross-sectional view as in FIG. 9 illustrating another enbodiment of the elastomeric tension-applying device incorporating the parts illustrated in FIGS. 10A and 10B.

FIG. 13 is a partial, perspective view, in partial cross section and partially cut away, illustrating another embodiment of the elastomeric tension-applying device shown in FIGS. 8-12 in which the attachment between the tension-applying device and the rigid arm is in the form of a releasable fastener.

FIG. 14 is a top cross-sectional view as in FIG. 9 illustrating the elastomeric tension-applying device of FIG. 13 attached to the rigid arm shown in FIGS. 5 and 6.

DETAILED DESCRIPTION OF THE INVENTION

Figure 1:
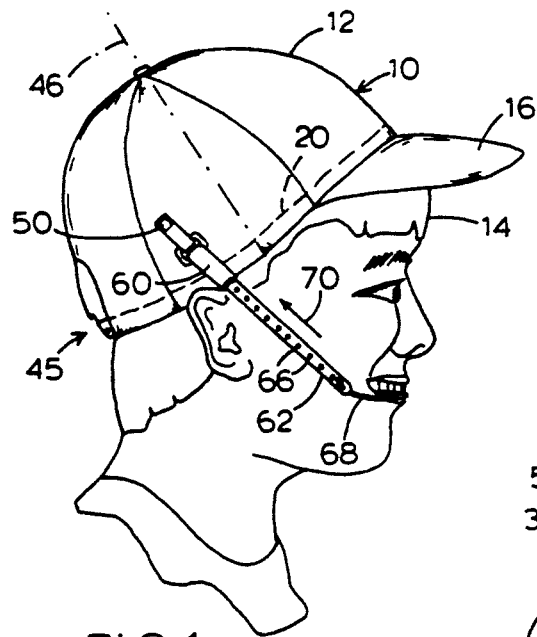
FIG. 1 is a side elevational view of a first embodiment of an anatomical head-worn device in accordance with the present invention, in the form of a cap, shown in place on the head of a user with a tension-applying device attached to the dome portion of the cap.

Referring to FIG. 1, the present invention is an anatomical head-worn device in the form of a cap 10 with a dome 12 for covering the top of a wearer's head 14. Cap 10 includes a stiff or semi-stiff bill 16 extending outwardly from the dome along a portion of its lower perimeter 17. Such caps are commonly referred to as bill caps or baseball caps. Extending around the inside of the cap along its lower perimeter 17 is a head-encircling band 20, shown in phantom in FIGS. 2 and 4. In part, band 20 serves the typical function of a hat-band, absorbing moisture and helping to retain cap 10 on the head. Band 20 preferably includes an adjustable portion 22 at the back of the cap, incorporating overlapping tabs 24, 26. Tab 24 is provided with openings 28 at regular intervals along its longitudinal length. Cooperating projections, or pins, 30 are formed on tab 26 for entering and engaging openings 28 to lock the tabs together at selected relative positions, in a manner well known in the art.

Adjustable portion 22 of band 20 permits adjustment of the circumferential length of band 20 to ensure a snug fit about the head of the user. A semi-circular opening 29 in the back of the dome 12, opposite bill 16, accommodates changes in the length of band 20. When the cap is worn as shown in FIG. 1, band 20 extends around the ovate contour of the head, encircling the head above the ears and crossing the front of the head at or above the forehead and extending around the back of the head below the posterior cranial convexity. That is a typical, comfortable position for wearing a bill cap. When the cap is properly sized, it fits snugly against the head to inhibit rotational slippage of the cap relative to the head.

Figure 2:
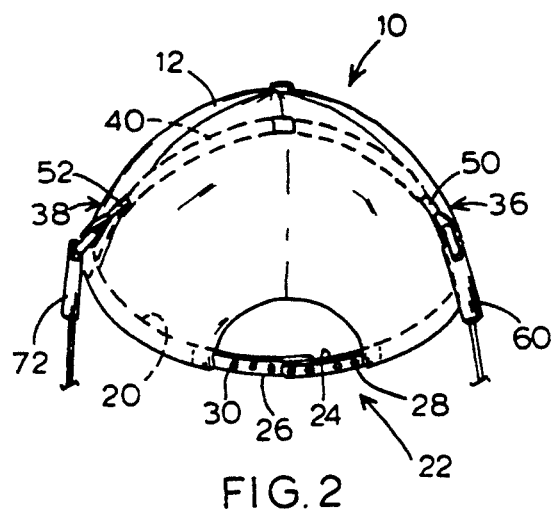
FIG. 2 is a partial, rear elevational view of the device of FIG. 1 illustrating in phantom the load-bearing strap mounted within the dome of the cap, and also illustrating, partially in phantom, the head-encircling band on the cap.
Figure 3:
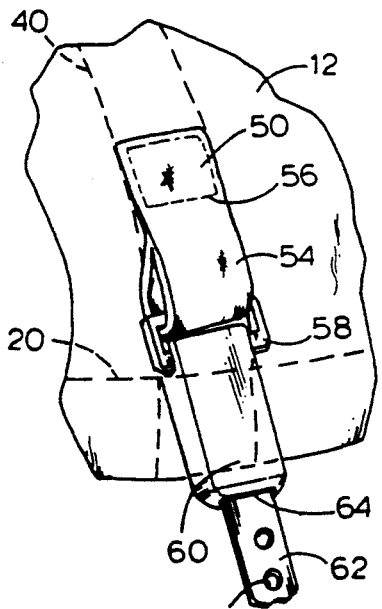
FIG. 3 is a partial view, on an enlarged scale, of a tension-device anchor for use on the cap shown in FIGS. 1 and 2.
Figure 4:
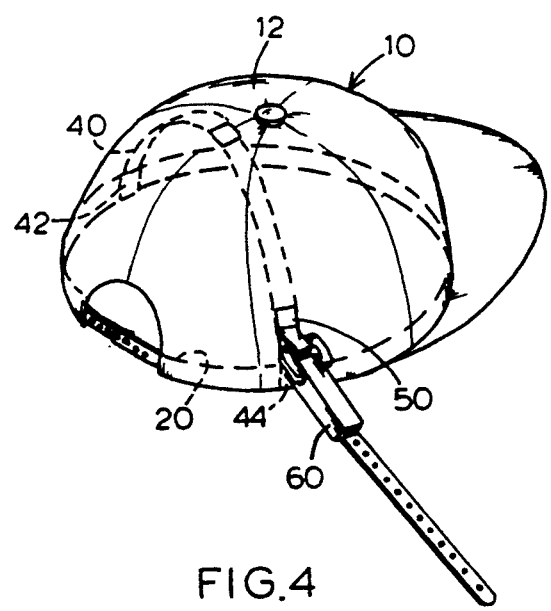
FIG. 4 is a side perspective view of the device shown in FIGS. 1 and 2, illustrating in phantom the locations of the head-encircling band and the load-bearing strap relative to the dome of the cap.

In the first embodiment of the invention shown in FIGS. 1-4, cap 10 is provided with a load-bearing strap which extends beneath dome 12 between the respective right and left sides 36, 38 of the cap. The two sides of the cap extend along the temples of the head when the cap is worn. Load-bearing strap 40, shown most clearly (in phantom) in FIGS. 2 and 4, is attached to the cap within the dome 12 for reactive-force engagement with the head. Strap 40 extends over the top of the wearer's head. It is operatively joined to band 20 at its two ends 42, 44, or to the fabric of dome 12, at points near or adjacent band 20, where the ends 42, 44 of strap 40 overlap or are adjacent to the band. Strap 40 is preferably positioned slightly back from the center line 46 of the cap as it extends over the top of the head (the center line 46 being located midway between the front end of the cap, where bill 16 is attached, and the back end of the cap 45, where adjustable band portion 22 is located). A third point of attachment between strap 40 and cap 10 is preferably provided near the top of dome 12 by a pattern of stitching 47 between the fabric of the strap and the fabric of the dome. The upper point of attachment, at 47, helps position the strap within the dome.

Tension-device anchors are provided on cap 10 for accommodating the attachment thereto of orthodontic tension-applying devices. In FIGS. 1-4, two tension-device anchors 50, 52 are provided respectively on the right and left sides 36, 38 of cap 10. FIG. 3 shows tension-device anchor 50 on an enlarged scale. Each anchor herein is in the form of a fabric loop 54 which is load-transmittingly attached to strap 40 through the fabric of the dome 12 by stitching 56 or by another suitable attachment method. A "C"-shaped shackle 58 passes through loop 54 and engages the sides of a spring-type orthodontic tension-applying device 60. Such tension-applying devices have an internal spring which applies a predetermined tension force to a plastic strip 62 extending from a slot 64 in one end of the device. Referring to FIG. 1, plastic strip 62 includes a plurality of holes 66 along its length for attachment of an orthodontic bow 68, or other orthodontic appliance, such appliances being well known in the art of orthodontic dentistry.

Tension-applying device 60 is designed to exert a tension force upwardly along strip 62 in the direction of arrow 70. The strip, in turn, applies an orthodontic force to the mouth via bow 68. Tension-device anchors 50, 52 are attached through dome 12 to strap 40 in a manner which causes the reactive force resulting from application of orthodontic forces to be applied predominately against the load-bearing strap. In other words, orthodontic forces applied in direction 70 are reacted against the head of the wearer via the strap. Strap 40 preferably has a slightly shorter length than the length of the adjacent inside surface of the fabric of dome 12 so that the load is carried by the strap rather than by the fabric of the dome. In that way, except at the points where strap 40 is attached to the cap, the strap provides reactive force engagement with the head in a manner non-deforming to dome 12, thus giving the cap a "normal" appearance.

Assuming tension is to be applied on both sides of the head, a tension-applying device is attached to each of the two anchors 50, 52 on opposite sides of cap 10. Each of the tension-applying devices 60, 72 shown in FIG. 2 can be separately calibrated to apply a different selected orthodontic tension force. Thus, cap 10 provides a means for applying selected,differentiated orthodontic tension forces on opposite sides of the head. Alternatively, cap 10 can be used to anchor a single orthodontic tension-applying device for directing an orthodontic corrective force to only one side of the dental region of the head. That can be done by installing a conventional orthodontic "J" hook on strip 62 of tension-applying device 60. The "J" hook (not shown) would replace bow 68 in FIG. 1 and extend around and into the mouth for direct attachment to an orthodontic mouth-worn appliance (not shown) in the manner well known in the art of orthodontic dentistry. Because cap 10 provides a secure, stable anchor point for reacting orthodontic tension forces against the head, it is ideally suited to direct orthodontic forces against only one side of the mouth.

Referring to FIG. 5, an alternative embodiment of the invention is shown in partial cross section. All of the elements of the first embodiment shown and identified in FIG. 1, except tension-device anchor 50 and the tension-applying devices attached thereto, are repeated in the second embodiment of the invention shown in FIGS. 5 and 6, and the reference numbers are repeated for like parts. In this second embodiment, a rigid arm 80, made herein of transparent plastic, is mounted on bill 16 at a predetermined angular relationship to the bill. Arm 20 is for extending downwardly in front of the face 82 when the cap is worn with the bill extending forwardly, as shown in FIG. 5. The arm is integrally attached to a mounting plate 84 at its upper end (see FIG. 6). A gusset 86 strengthens the attachment between arm 80 and mounting plate 84. Plural anchor points 88, such as rivets, are used to attach mounting plate 84 to bill 16. The bill is formed of fabric-covered paperboard, or of another suitable stiff or semi-stiff sheet material. A rigid, or semi-rigid, thin intermediate plate 90, positioned between mounting plate 84 and bill 16, helps strengthen the bill against deformation.

Arm 80 is approximately two and a half inches wide at its lower end 91. It includes a central opening 92, as shown in FIG. 6, which divides the arm into two, spaced-apart, generally vertical members 94, 96 which are joined at their upper ends to define an inverted "Y"-shape. The vertical members are joined together at their respective lower, or distal, ends by a cross member 98, which completes the encirclement of opening 92. Each vertical member 94, 96 serves as an anchor point for an orthodontic tension-applying device. A flexible, or elastic, connecting tie 100 is secured to the lower end of right-side member 96, and another tie 104 is attached to the lower end of left-side member 94. Each tie 100, 104 applies a protractive tension force in the direction of arrow 102 (FIG. 5). Ties 100, 104 include, or are connected to, elastic bands or the like which are, in turn, coupled to orthodontic appliances in the mouth (not shown), such appliances being well known in orthodontics.

Like the first embodiment, the second embodiment of FIGS. 5 and 6 is able to direct different orthodontic forces to selected areas of the mouth. Tension-applying devices calibrated to exert different tension forces can be attached to members 94 and 96. In that way, different forces can be applied on the right and left sides of the mouth. As long as cap 10 is properly sized to fit snugly against the head, as described in the first embodiment, it will inhibit rotational slippage of the cap relative to the head, and will allow for the application of differential orthodontic forces on opposite sides of the head. An optional means of stabilizing arm 80, to allow for the application of additional orthodontic force, is provided by a semi-rigid fulcrum member 105 (indicated in phantom in FIG. 5) which can be fitted around the upper end of arm 80. Fulcrum member 105 extends between arm 80 and the forehead of the wearer, providing an additional point at which the force applied by the orthodontic devices can be reacted against the head.

In yet another alternative embodiment, the present invention can incorporate both the tension-device anchors 50, 52 from the first embodiment and the downwardly-extending rigid arm 80 of the second embodiment. Such a configuration of the invention allows the orthodontist great flexibility in directing orthodontic forces as needed to make orthodontic corrections. For example, if there is a need to apply a retractive force in the direction of arrow 70 (FIG. 1) on the right side of the head, and a protractive force in direction of arrow 102 (FIG. 5) on the left side of the head, a cap incorporating all the elements of FIGS. 1-6 can produce such a differential force configuration. A properly sized cap 10 will resist rotational displacement sufficient to apply such differential forces.

Another embodiment of the invention is illustrated in FIG. 7. In this embodiment, cap 10 includes all of the element of the first embodiment shown in FIG. 1, except tension-device anchor 50 and the tension-applying devices attached thereto, and the reference numbers from FIG. 1 are repeated for like parts. In the embodiment of FIG. 7, one or more tension-device anchors 110 is (are) attached to the bill 16 of cap 10. Illustrated anchor 110 is preferably attached to bill 16 by means of a rivet 112, or similar device, which permits the anchor to swivel about its point of attachment. A piece of fabric 114, through which rivet 112 extends, serves as a support for a loop 116, which is identical with loop 54 in FIG. 3. The other parts of the tension-device anchor are the same as those shown in FIG. 3, including a spring-loaded, tension-applying device 118 for applying tension in the direction of arrow 120 via a plastic strip 122. In the embodiment of FIG. 7, the cap will generally be worn backwards with the bill 16 extending over the back of the neck. It could alternatively be used to direct orthodontic force upwardly from the mouth by wearing the cap with the bill extending forwardly, as shown in FIG. 1. In the embodiment of FIG. 7, load-bearing strap 40 can be omitted from the inside of the dome 12 of cap 10.

Still another embodiment of the invention is illustrated in FIGS. 8 and 9, which are partial views, slightly enlarged, of the bottom portion of rigid arm 80, shown in FIGS. 5 and 6. In the embodiment of FIGS. 8 and 9, a non-positive attachment is provided between a different type of tension-applying device 130, described below, and rigid arm 80. The purpose of using a non-positive engagement between an orthodontic tension-applying device and the rigid arm is to provide for immediate disengagement of the tension-applying device from the arm in the event of a mishap involving cap 10 or tension-applying device 130. Such a mishap would include another person bumping or grabbing the cap and exerting a large outward force on arm 80, or the arm or tension-applying device becoming entangled in another object. Such a mishap could injure the wearer. To prevent such a possibility, tension-applying device 130 is not directly attached to arm 80 but engages the arm in a manner which retains the device on the arm when orthodontic tension force is being applied.

Referring to FIGS. 8 and 10A, the orthodontic tension-applying device 130 is in the form of a unitary elastomeric band which extends around vertical members 94, 96 of rigid arm 80, near the cross member 98 at the bottom of the arm. FIG. 8 illustrates shallow notches 131 formed in members 94, 96 to help position device 130 relative to arm 80. Tension-applying device 130, which serves the same function as tension-applying device 60, 62 in FIG. 1, is made of the same elastomeric material used to form strip 62. Elastomeric tension-applying device 130, also referred to as elastomeric member 130, is a unitary piece of elastomeric material formed in several distinct, integral segments, each segment having a substantially different cross section, shape and function. The first segment 140 of elastomeric member 130 is wide and flat, with a generally rectangular cross section, designed to extend around members 94, 96. FIG. 10A, shows a terminal end portion of elastomeric member 130 on an enlarged scale. End portion 141 of the tension-applying device 130, is the part which enters the mouth of the wearer. End 141 includes a first segment 140, a second segment 145, in which elastomeric member 130 transitions to a second, generally rounded cross section, and a third segment 148 consisting of terminal links. In the embodiment of FIGS. 8 and 9, elastomeric member 130 includes two of the end portions 141, at opposite ends of the elastomeric member. The purpose of the transitional second segment 145 of each end portion is to provide a smaller, rounded, cross section where the elastomeric member enters the mouth of the wearer. The generally rounded or circular cross section of the second segment minimizes irritation to the corners of the mouth caused by the elastomeric member. Terminal links 148 are conventionally used in orthodontic dentistry to connect tension-applying devices to mouth-worn appliances.

FIG. 9 is a top view, in partial cross section, further illustrating the embodiment of FIG. 8. First segment 140 of the elastomeric member 130 extends around both members 94, 96 of rigid arm 80. The tension exerted between the rigid arm 80 and the dental region of the wearer which is receiving orthodontic correction tends to hold the elastomeric member against the rigid arm. Shallow positioning grooves or notches 131 are provided on arm members 94, 96 to help position the elastomeric member on the arm.

An alternative version of the device 130 shown in FIGS. 8 and 9 is shown in FIGS. 10A and 10B. The elastomeric member end 141, shown in FIG. 10A, is combined with a hook formed integrally with first segment 140, shown in FIG. 10B, to form a single-ended elastomeric member 154, also shown in FIG. 11. Hook 156 is designed to engage one of the members 94, 96 of arm 80 in the manner shown in FIG. 11, allowing for use of only a single tension-applying device on the rigid arm. Like the embodiment of FIGS. 8 and 9, the hook is not directly attached to arm 80 but engages the arm in a manner which retains the elastomeric device on the arm when orthodontic tension force is being applied by member 154. Hook 156 is a non-clamping, open-sided device for extending around one of the upright members 94, 96 and is held in place by an exertion of force in the direction of arrow 157 (see FIG. 11). The terminal end of elastomeric member 154 is the same as terminal end 141 shown in FIG. 10A and described above with reference to FIGS. 8, 9 and 10A.

An additional embodiment of the invention is illustrated in FIG. 12, in which elastomeric member 159 includes a hook 156 and terminal end 141 as shown in FIGS. 10A, 10B and 11, but which has a substantially longer wide, flat, first segment to permit the application of orthodontic tension force on the side of the wearer's mouth adjacent member 96 of rigid arm 80 while hooking the elastomeric member around member 94. The wide, flat first segment is extended from hook 156 across the arm 80 and around member 96, the hook being retained in the same manner as hook 156 in the embodiment of FIG. 11.

Another unitary embodiment of the elastomeric orthodontic tension-applying device 130 of FIG. 8 is illustrated in FIGS. 13 and 14. In this embodiment, segment 140 of an elastomeric member 160 is releasably attached to rigid arm 80 by means of an elastomeric fastener 162. Fastener 162 is in the form of a wrap-around loop 164 which terminates in an eyelet opening 166, and a second strip of material 170 which terminates in an elastomeric ball 172 sized to fit with some resistance through opening 166. Ball 172 and opening 166 together form a fastener which can be tailored to separate and release the elastomeric member from rigid arm 80 if a predetermined tension force, exerted by elastomeric member 160 in the direction of arrow 174, is exceeded. Like the other embodiments so far described, the embodiment of FIGS. 13-14 is designed to release the orthodontic tension force in the event of a mishap with cap 10 which would otherwise exert excessive forces on the mouth of the wearer.

The present invention provides a more socially acceptable head-worn device for attachment of exterior orthodontic appliances to the head, in comparison with the prior art. Bill caps are attractive and popular, and they provide an excellent force base against which orthodontic forces can be reacted to the head. In fact, the bill cap proposed herein is superior to prior art, orthodontic, head-worn devices in allowing different forces to be applied on different sides of the head over a wide range of selectable directions. The second embodiment of the invention, which incorporates downwardly-extending rigid arm 80, is substantially more comfortable to wear than prior art face masks, when protractive force is required, because there is no application of force directly to the face or chin of the wearer. Caps in accordance with the present invention can be made in bright colors and/or can include the names and logos of school or sports teams, adding to their social acceptability. As a consequence, children and others who need to wear external orthodontic devices will more readily accept them, and such acceptance, of course, will promote and increase the benefits of orthodontic dentistry.

What is claimed is:

1. An anatomical head-worn device for application of an orthodontic tension force, comprising:
   a bill cap with a dome for covering the top of the head and a bill extending outwardly from the dome along a portion of its perimeter, the cap being sized to fit snugly against the head to inhibit rotational slippage relative to the head,
   an elongate load-bearing strap joined to said cap on the inside of said dome, said strap being shorter in length than the length of the adjacent inside surface of said dome and extending in a run between its ends which is spaced from said surface, and
   an orthodontic tension-device anchor on said cap for accommodating the attachment thereto of an orthodontic tension-applying device in a manner which causes the orthodontic force applied to be reacted against the head via said cap and said strap.

2. An anatomical head-worn device as in claim 1 including at least two tension-device anchors on said cap attached to said strap each of which accommodates attachment of a separate orthodontic tension-applying device.

3. An anatomical head-worn device as in claim 1 in which said strap is jointed to said cap in a manner which is non-deforming to the dome when orthodontic force is being applied by the device.

4. An anatomical head-worn device as in claim 1 in which said tension-device anchor is attached to said cap in a manner which causes the reactive force resulting from application of the orthodontic force to be applied predominately against said load-bearing strap.

5. An anatomical head-worn device as in claim 1 in which said tension-device anchor is attached to said bill.

6. An anatomical head-worn device as in claim 5 in which said tension-device anchor includes a rigid arm mounted on said bill for extending downwardly in front of the face, when the cap is worn with the bill extending forwardly, permitting the attachment of a tension-applying device to said arm in a manner which causes the orthodontic force applied to be reacted against the head via said arm and cap.

7. An anatomical head-worn device as in claim 1 in which said strap extends over the top of the head of the wearer, and including a head-encircling band for extending around the ovate contour of the head along the lower margin of the cap, said strap being operatively joined at its ends to said band.

8. An anatomical head-worn device for application of an orthodontic tension force, comprising:
   a cap with a dome for covering the top of the head,
   a load-bearing strap mounted on the cap within the dome for reactive force engagement with the head, said strap being shorter in length than the length of the adjacent inside surface of the dome such that force is reacted against said strap in a manner non-deforming to the dome,
   a head-encircling band for extending around the ovate contour of the head along the lower margin of the cap, said band being sized to fit snugly around the head to inhibit rotational slippage of the cap relative to the head, and
   a tension-device anchor load-transmittingly connected to said strap for accommodating the attachment of a tension-applying device in a manner which causes the orthodontic force applied to be reacted against the head predominately via said strap.

9. An anatomical head-worn device as in claim 8 in which said cap has opposed sides which extend along the temples when the cap is worn, including two said tension-device anchors load-transmittingly connected to said strap, one on each side of said cap.

10. An anatomical head-worn device as in claim 9 in which the load-bearing strap is operatively joined at its ends to said head-encircling band on each side of the cap, and said tension-device anchors are connected to said cap adjacent the ends of said load-bearing strap.

11. An anatomical head-worn device as in claim 8 in which said cap is a bill cap having a bill extending outwardly therefrom along a portion of its perimeter.

12. An anatomical head-worn device for application of an orthodontic tension force, comprising:
   a bill cap with a dome for covering the top of the head and a bill extending outwardly from the dome along a portion of its perimeter, and
   a tension-device anchor on said cap, including a rigid arm mounted on said bill which extends downwardly in front of the face when the cap is worn with the bill extending forwardly, and
   an orthodontic tension-applying device extending between said rigid arm and the dental region of the wearer for applying an orthodontic force to effect an orthodontic correction, whereby the orthodontic force applied is reacted against the head via said rigid arm, said bill and said cap.

13. An anatomical head-worn device for application of an orthodontic tension force, comprising:
   a bill cap with a dome for covering the top of the head and a bill extending outwardly from the dome along a portion of its perimeter,
   a tension-device anchor on said cap, including an arm having opposed first and second ends, said arm being mounted on said bill at its first end extending downwardly in front of the face, when the cap is worn with the bill extending forwardly, and with a predetermined angular relationship between said arm and said bill, and
   at least two orthodontic tension-applying devices attached to said arm adjacent said second end, each said tension-applying device exerting tension between said arm and the dental region of the wearer receiving orthodontic correction, whereby different orthodontic forces are directed to selected areas by said tension-applying devices and said forces are reacted against the head via said rigid arm, said bill and said cap.

14. An anatomical head-worn device as in claim 13 in which said orthodontic tension-applying devices exert different tensile forces relative to one another, whereby orthodontic forces can be selectively exerted against selected areas of the head.

15. An anatomical head-worn device for application of an orthodontic tension force, comprising:
   a bill cap with a dome for covering the top of the head and a bill extending outwardly from the dome along a portion of its perimeter,
   a tension-device anchor on said cap, including a rigid arm mounted on said bill for extending downwardly in front of the face, when the cap is worn with the bill extending forwardly, the arm accommodating the application of an orthodontic force by an orthodontic tension-applying device which exerts tension between said rigid arm and the dental region of the wearer receiving orthodontic correction, whereby the orthodontic force applied is reacted against the head via said rigid arm, said bill and said cap, and
   means for effecting a non-positive engagement between an orthodontic tension-applying device and said rigid arm, whereby the tension-applying device will disengage from the rigid arm and release the orthodontic tension force in the event of a mishap involving the anatomical head-worn device.

16. An anatomical head-worn device as in claim 15 in which said means for effecting a non-positive engagement includes a hook on a tension-applying device for catching and holding said rigid arm.

17. An anatomical head-worn device for application of an orthodontic tension force, comprising:
   a bill cap with a dome for covering the top of the head and a bill extending outwardly from the dome along a portion of its perimeter, and
   a tension-device anchor on said cap, including a rigid arm mounted on said bill which extends downwardly in front of the face, when the cap is worn with the bill extending forwardly, and
   an orthodontic tension-applying device operatively connected between said rigid arm and an orthodontic corrective appliance for applying an orthodontic force between said rigid arm and the dental region of the wearer, said tension-applying device including an elastomeric member which applies orthodontic force when stretched, the force being reacted against the head via said rigid arm, said bill and said cap.

18. An anatomical head-worn device for application of an orthodontic tension force, comprising:
   a bill cap with a dome for covering the top of the head and a bill extending outwardly from the dome along a portion of its perimeter,
   a tension-device anchor on said cap, including a rigid arm mounted on said bill for extending downwardly in front of the face, when the cap is worn with the bill extending forwardly,
   an orthodontic tension-applying device engageable with said rigid arm for applying an orthodontic force between said rigid arm and the dental region of the wearer for the purpose of orthodontic correction, whereby the force exerted by said elastomeric member is reacted against the head via said rigid arm, said bill and said cap, and said tension-applying device including an elastomeric member which applies orthodontic force when stretched, said elastomeric member being an elongate strip of elastomeric material, including a first segment for engaging said rigid arm, said first segment having a first cross section, and including a second segment in which the elastomeric member transitions to a second cross section, smaller than said first cross section, for entering the mouth of the wearer, whereby the smaller cross section of said second segment minimizes irritation of the mouth of the wearer.

19. An anatomical head-worn device as in claim 18 in which said second cross section of said second segment has a generally curvilinear cross-sectional outline.

20. An anatomical head-worn device as in claim 19 in which said non-positive engagement includes a hook secured to said first segment of said orthodontic tension-applying device for catching and holding said rigid arm as long as tension is exerted against said hook by said tension-applying device, and for releasing said rigid arm when tension is released.

21. An anatomical head-worn device as in claim 18 in which said second cross section of said second segment has a generally rounded cross-sectional outline.

22. An anatomical head-worn device as in claim 18 including a non-positive engagement between said first segment of said orthodontic tension-applying device and the rigid arm, whereby said first segment will disengage from the rigid arm and release the orthodontic tension force in the event of a mishap with the anatomical head-worn device.

23. An anatomical head-worn device as in claim 18 in which said second segment is releasably attached to said rigid arm by a fastener which will separate said first segment from said rigid arm if a predetermined tension force is exerted on the fastener.

* * * * *